United States Patent [19]

Nagata et al.

[11] Patent Number: 5,302,749

[45] Date of Patent: Apr. 12, 1994

[54] STABILIZING METHOD OF ISOCYANATE COMPOUNDS AND ISOCYANATE COMPOSITIONS STABILIZED THEREBY

[75] Inventors: Teruyuki Nagata; Hiroyuki Yamashita; Masahiko Kusumoto; Koju Okazaki, all of Ohmuta, Japan

[73] Assignee: Mitsui Toatsu Chemicals, Incorporated, Tokyo, Japan

[21] Appl. No.: 852,724

[22] Filed: Mar. 17, 1992

[30] Foreign Application Priority Data

Mar. 19, 1991 [JP] Japan .................................. 3-054275

[51] Int. Cl.$^5$ ............................................ C07C 263/18
[52] U.S. Cl. ..................................... 560/333; 524/323
[58] Field of Search ........................... 560/333; 524/323

[56] References Cited

U.S. PATENT DOCUMENTS

T881,001  12/1970  Werts, III et al. .................. 252/182
3,715,381  2/1973  Spaunburgh et al. ............... 560/333

FOREIGN PATENT DOCUMENTS 1595699  9/1969  Fed. Rep. of Germany .
1147451  11/1957  France .
46-27594  8/1971  Japan .
51-48619  4/1976  Japan .
59-98050  6/1984  Japan .
934458  8/1963  United Kingdom .

*Primary Examiner*—Jose' G. Dees
*Assistant Examiner*—Vera C. Clarke
*Attorney, Agent, or Firm*—Burns, Doane, Swecker & Mathis

[57] ABSTRACT

A method for stabilizing an isocyanate compound by adding 10–5000 ppm of phenol to the isocyanate compound, and also an isocyanate composition so stabilized. In the isocyanate composition stabilized by the above method, coloring due to time-dependent changes and the occurrence of turbidity through self-polymerization are both suppressed so that it shows outstanding storage stability compared with a corresponding isocyanate composition containing a conventional stabilizer.

6 Claims, No Drawings

STABILIZING METHOD OF ISOCYANATE COMPOUNDS AND ISOCYANATE COMPOSITIONS STABILIZED THEREBY

BACKGROUND OF THE INVENTION

1) Field of the Invention

The present invention relates to a stabilizing method of isocyanate compounds to suppress both yellowing and the occurrence of turbidity, which would otherwise take place due to changes along the passage of time and also to isocyanate compositions stabilized by the above method. The isocyanate compositions according to the present invention are particularly useful as raw materials for optical urethane resins for plastic lenses and the like, which resins are required to have colorless transparency.

2) Description of the Related Art

Isocyanate compounds are accompanied by the drawback that, because of the high reactivity exhibited by each isocyanato group thereof, they lack stability and tend to undergo coloring and/or self-polymerization during storage. Addition of a stabilizer is indispensable to suppress coloring and self polymerization.

Various compounds have heretofore been known as stabilizers for isocyanate compounds. Representative ones among them are phenols such as 2,6-di-tert. butyl-p-cresol (U.S. Pat. No. 3,715,381) and phosphite esters such as triphenyl phosphite (Japanese Patent Publication No. 33438/1970). In addition, many other stabilizers have also been known, including ureas, carbamates, acid amides (Japanese Patent Publication No. 7044/1970, Japanese Patent Laid-Open No. 36546/1975); acid substances such as perchloric acid and trifluoromethanesulfonic acid (German Patent Publication No. 2,837,770); carbon dioxide and sulfur dioxide (U.S. Pat. No. 3,247,236); organic amines (Japanese Patent Laid-Open No. 101344/1975); acid chlorides (Japanese Patent Laid-Open No. 179917/1988); siloxanes (Belgian Patent Publication No. 858,921); organotin compounds (European Patent Publication No. 203,874); and acyl isocyanate compounds (Japanese Patent Publication No. 3825/1973).

Known examples of phenolic stabilizers useful in the practice of the present invention include pyrogallol, catechol, guaiacol, eugenol, pentachlorophenol (Japanese Patent Publication No. 3825/1973, Japanese Patent Publication No. 7044/1970), 2,6-di-tert. butyl-p-cresol and methacresol (Japanese Patent Laid-Open No. 48619/1976), as well as alkyl-substituted phenols and bisphenols (Japanese Patent Publication No. 27,594/1971, Polish Patent Publication No. 100,154, British Patent Publication No. 1,315,520, U.S. Pat. No. 3,682,902, Japanese Patent Laid-Open No. 98050/1984).

It is, however, still difficult to suppress both the coloring and self-polymerization-induced turbiding of isocyanate compounds even by these stabilizers. Satisfactory results have not yet been obtained.

It is known that aliphatic polyisocyanates, particularly xylylene diisocyanate tend to become turbid due to the formation of a 1-nylon-type polymer through self-polymerization [Journal of the Chemical Society, 82, 866 (1960)]. It has therefore been found that the stabilizers disclosed in such patent publications do not permit stable storage over 3 months or longer at room temperature.

There is hence an outstanding demand for the development of a stabilizer which can suppress both yellowing and turbiding of isocyanate compounds over a long period of time.

SUMMARY OF THE INVENTION

A first object of the present invention is to provide a stabilizing method of isocyanate compounds by suppressing both yellowing and the occurrence of turbidity over a long period of time; and second object of the present invention is to provide isocyanate compositions stabilized by the above method.

As a result of an extensive search of stabilizers for isocyanate compounds, the present inventors have found that phenols are comparatively effective and, among them, phenol shows outstanding effects for the suppression of coloring and turbidity. Even xylylene diisocyanate, which is particularly unstable, can be stored over 6 months or longer at 20° C. by the addition of phenol. It has already been known that phenols are effective as stabilizers, however, such an outstanding stabilizing effect of phenol, which is the simplest compound among them, has not been known at all to date.

In one aspect of the present invention, there is thus provided a stabilizing method of an isocyanate compound, which comprises adding 10–5000 ppm of phenol to the isocyanate compound.

In another aspect of the present invention, there is also provided an isocyanate composition obtained by adding 10–5000 ppm of phenol to an isocyanate compound.

DETAILED DESCRIPTION OF THE INVENTION

It is desirable to add phenol to an isocyanate compound in an amount of 10–5000 ppm, with 100–2000 ppm being more preferred. Amounts smaller than 10 ppm are too little to exhibit the stabilizing effect sufficiently. Amounts greater than 5000 ppm, on the other hand, may aggravate the coloring of the isocyanate compound in some instances. Amounts outside the above range are therefore not preferred.

Examples of the isocyanate compound to which phenol can be added as a stabilizer include monoisocyanate compounds and polyisocyanate compounds. Illustrative of the former compounds include methyl isocyanate, butyl isocyanate, phenyl isocyanate and benzyl isocyanate.

Examples of the latter compounds, on the other hand, include aliphatic polyisocyanates such as ethylene diisocyanate, trimethylene diisocyanate, tetramethylene diisocyanate, hexamethylene diisocyanate, octamethylene diisocyanate, nonamethylene diisocyanate, 2,2'-dimethylpentane diisocyanate, 2,2,4-trimethylhexane diisocyanate, decamethylene diisocyanate, butene diisocyanate, 1,3-butadiene-1,4-diisocyanate, 2,4,4-trimethylhexamethylene diisocyanate, 1,6,11-undecane triisocyanate, 1,3,6-hexamethylene triisocyanate, 1,8-diisocyanato-4-isocyanatomethyloctane, 2,5,7-trimethyl-1,8-diisocyanato-5-isocyanato methyloctane, bis-(isocyanatoethyl)carbonate, bis(isocyanatoethyl)ether, 1,4-butyleneglycol dipropylether-$\alpha,\alpha'$-diisocyanate, methyl lysinediisocyanate, lysine triisocyanate, 2-isocyanatoethyl 2,6-diisocyanatohexahoate, 2-isocyanatopropyl 2,6-diisocyanatohexanoate, xylylene diisocyanate, bis-(isocyanatoethyl)benzene, bis-(isocyanatopropyl)benzene, $\alpha,\alpha,\alpha',\alpha'$-tetramethylxylylene diisocyanate, bis(isocyanatobutyl)benzene, bis-(isocyanatomethyl)naphthalene, bis(isocyanatomethyl)- diphenylether, bis-(isocyanatoethyl)phthalate, mesitylene triisocyanate, 2,6-di(isocyanatomethyl)furan, isophorone diisocyanate, bis(isocyanatomethyl)cyclohexane, dicyclohexylmethane diisocyanate, cyclohexane diisocyanate, methylcyclohexane diisocyanate, dicyclohexyldimethylmethane diisocyanate, 2,2'-dimethyldicyclohexylmethane diisocyanate, bis(4-isocyanato-$n$-butyliene)pentaerythritol, dimer acid diisocyanates, 2-isocyanatomethyl-3-(3-isocyanatopropyl)-5-isocyanatomethylbicyclo[2.2.1]heptane, 2-isocyanatomethyl-3-(3-isocyanatopropyl)-6-isocyanatomethyl-bicyclo[2.2.1]-heptane, 2-isocyanatomethyl-2-(3-isocyantopropyl)-5-isocyanatomethyl-bicyclo[2.2.1]heptane, 2-isocyantomethyl-2-(3-isocyanatopropyl)-6-isocyanatomethylbicyclo[2.2.1]heptane, 2-isocyanatomethyl-3-(3-isocyanatopropyl)-5-(2-isocyanatoethyl)bicyclo[2.2.1]-heptane, 2-isocyanatomethyl-3-(3-isocyanatopropyl)-6-(2-isocyanatoethyl)-bicyclo[2.2.1]heptane, 2-isocyanatomethyl-2-(3-isocyantopropyl)-5-(2-isocyanatoethyl)-bicyclo[2.2.1]heptane, 2-isocyanatomethyl-2-(3-isocyanatopropyl)-6-(2-isocyanatoethyl)-bicyclo[2.2.1]heptane, 2,5(or 6)-bis-(isocyanatomethyl)bicyclo[2.2.1]heptane, thiodiethylene diisocyanate, thiodipropyl diisocyanate, thiodihexyl diisocyanate, dimethylsulfone diisocyanate, dithiodimethyl diisocyanate, dithiodiethyl diisocyanate and dithiodipropyl diisocyanate; and aromatic polyisocyanates such as phenylene diisocyanate, tolylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, naphthalene diisocyanate, methylnaphthalene diisocyanate, biphenyl diisocyanate, tolidine diisocyanate, 4,4'-diphenylmethane diisocyanate, 3,3'-dimethyldiphenylmethane-4,4'-diisocyanate, dibenzyl-4,4'-diisocyanate, bis(isocyanatophenyl)ethylene, 3,3'-dimethoxybiphenyl-4,4'-diisocyanate, triphenylmethane triisocyanate, polymeric MDI, naphthalene triisocyanate, diphenylmethane-2,4,4'-triisocyanate, 3-methyldiphenylmethane-4,6,4'-triisocyanate, 4-methyldiphenylmethane-3,5,2',4',6'-pentaisocyanate, phenylisocyanatomethyl isocyanate, phenylisocyanatoethyl isocyanate, tetrahydronaphthalene diisocyanate, hexahydrobenzene diisocyanate, hexahydrodiphenylmethane-4,4'-diisocyanate, diphenylether diisocyanate, ethyleneglycol diphenylether diisocyanate, 1,3-propyleneglycol diphenyletherdiisocyanate, benzophenone diisocyanate, diethyleneglycol diphenylether diisocyanate, dibenzofuran diisocyanate, carbazole diisocyanate, ethylcarbazole diisocyanate, dichlorocarbazole diisocyanate; sulfide-bond-containing aromatic isocyanates, e.g., diphenylsulfide-2,4'-diisocyanate, diphenylsulfide-4,4'-diisocyanate, 3,3'-dimethoxy-4,4'-diisocyanatodibenzylthioether, bis(4-isocyanatomethylphenyl)sulfide and 4,4'-methoxyphenylthioethyleneglycol-3,3'-diisocyanate; disulfide-bond-containing aromatic isocyanates, e.g., diphenyldisulfide-4,4'-diisocyanate, 2,2'-dimethyldiphenyldisulfide-5,5'-diisocyanate, 3,3'-dimethyldiphenyldisulfide-5,5'-diisocyanate, 3,3'-dimethyldiphenyldisulfide-6,6'-diisocyanate, 4,4'-dimethyldiphenyldisulfide-5,5'-diisocyanate, 3,3'-dimethoxydiphenyldisulfide-4,4'-diisocyanate and 4,4'-dimethoxydiphenyldisulfide-3,3'-diisocyanate; sulfone-bond containing aromatic isocyanates, e.g., diphenyl-sulfone-4,4'-diisocyanate, diphenylsulfone-3,3'-diisocyanate, benzidinesulfone-4,4'-diisocyanate, diphenylmethanesulfone-4,4'-diisocyanate, 4-methyldiphenylsulfone-2,4'-diisocyanate, 4,4'-dimethoxydiphenylsulfone-3,3'-diisocyanate, 3,3'-dimethoxy-4,4'-diisocyanatobenzylsulfone, 4,4'-dimethyldiphenylsulfone-3,3'-diisocyanate, 4,4'-di-tert-butyldiphenylsulfone-3,3'-diisocyanate, 4,4'-methoxydiphenylethylenesulfone-3,3'-diisocyanate and 4,4'-dichlorodiphenylsulfone-3,3'-diisocyante; sulfonate-ester-bond-containing aromatic isocyanates, e.g., 4-methyl-3-isocyanatophenylsulfonyl-4'-isocyanatophenol ester and 4-methoxy-3-isocyanatophenylsulfonyl-4'-isocyanatophenol ester; and sulfonamide-bond-containing aromatic isocyanates, e.g., 4-methyl-3-isocyanatophenylsulfonylanilido-3'-methyl-4'-isocyanate, diphenylsulfonylethylenediamine-4,4'-diisocyanate, 4,4'-methoxyphenylsulfonyl-ethylenediamine-3,3'-diisocyanate and 4-methyl-3-isocyanatophenylsulfonylanilido-4-methyl-3'-isocyanate. Sulfur-containing heterocyclic compounds such as thiophene-2,5-diisocyanate and, further, 1,4-dithiane-2,5-diisocyanate can be mentioned as examples of polyisocyanate compounds.

In addition, phenol can also be added to isothiocyanato-containing isocyanate compounds. Their examples include aliphatic compounds such as 1-isocyanato-3-isothiocyanatopropane, 1-isocyanato-5-isothiocyanatopentane, 1-isocyanato-6-isothiocyanatohexane, isothiocyanatocarbonylisocyanate and 1-isocyanato-4-isothiocyanatocyclohexane; aromatic compounds such as 1-isocyanato-4-isothiocyanatobenzene and 4-methyl-3-isocyanato-1-isothiocyanatobenzene; heterocyclic compounds such as 2-isocyanato-4,6-diisothiocyanato-1,3,5-triazine; and compounds containing one or more sulfur atoms other than that contained in each isothiocyanato group, such as 4-isocyanato-4'-isothiocyanatodiphenylsulfide and 2-isocyanato-2'-isothiocyanatodiethyldisulfide.

In the stabilizing method of the present invention for an isocyanate compound, no particular limitation is imposed on the manner of addition of 10-5000 ppm of phenol to the isocyanate compound. It is, however, preferable to adjust the amount depending on the type of the isocyanate compound to be added with and its storage conditions such as the period, method and atmosphere of the storage.

Conventional stabilizers for isocyanate compounds can also be used in combination with phenol in the stabilized isocyanate composition of this invention insofar as they do not interfere with the effect of the present invention.

The isocyanate composition stabilized according to the present invention shows, as will be demonstrated in examples below, desired storage stability even at temperature conditions as high as 80° C.

The isocyanate composition added with 10-5000 ppm of phenol shows excellent storage stability as its coloring with the passage of time and the occurrence of turbidity through self-polymerization are both suppressed. For particularly-unstable xylylene diisocyanate, phenol shows outstanding stabilizing action compared with known stabilizers.

As shown in Table 2, the purity reduction of an isocyanate compound can be controlled by the addition of phenol. It exhibits marked effect for aliphatic polyisocyanates.

The present invention will hereinafter be described specifically by the following examples and comparative examples. It should however be borne in mind that this invention is by no means limited to or by the examples.

EXAMPLES 1-3 AND COMPARATIVE EXAMPLES 1-31

Portions of m-xylylene diisocyanate (purity: 99.8%; hydrolyzable chlorine: 0.010%; hue in accordance with Method 5.1 of JIS K1556: ApHA 10) were added, repsectively, with the stabilizers shown in Table 1. Each mixture was purged with nitrogen in a glass container. After hermetically sealed, the container was stored at 20° C. Visual observation of turbiding and the measurement of its APHA value were performed every week. The results are shown in Table 1.

The test period was at 24 max., although the test was stopped when turbiding was visually observed or when the APHA value exceeded 20.

EXAMPLES 4-12 AND COMPARATIVE EXAMPLE 32-40

Samples, which were free of phenol and added with 500 ppm of phenol, respectively were prepared from various isocyanate compounds having a purity of at least 99.8% and an APHA value of 10. They were each placed in a glass container, purged with nitrogen, hermetically sealed, and then stored at 80° C. A one-gram portion was collected from each sample every day and dissolved in 20 ml of toluene. The number of days until turbidity was observed was recorded. With respect to the samples in which turbidity was not observed 6 days or more, their APHA values and purity were measured on the 6th day and the test was conducted for 10 days at the maximum. The results are shown in Table 2.

TABLE 1

| No. | Stabilizer | Amount added (ppm) | Weeks until turbidity was visually observed | Weeks until ALPH value exceeded 20 |
|---|---|---|---|---|
| Example 1 | Phenol | 10 | >24 | >24 |
| Example 2 | Phenol | 500 | >24 | >24 |
| Example 3 | Phenol | 5000 | >24 | >24 |
| Comp. Ex. 1 | Phenol | 1 | 4 | |
| Comp. Ex. 2 | Phenol | 10000 | | 13 |
| Comp. Ex. 3 | Not added | 0 | 1 | |
| Comp. Ex. 4 | O-cresol | 500 | 4 | |
| Comp. Ex. 5 | M-cresol | 500 | 5 | |
| Comp. Ex. 6 | P-cresol | 500 | 3 | |
| Comp. Ex. 7 | 2,6-Ditertiarybutyl-p-cresol | 500 | 8 | |
| Comp. Ex. 8 | Eugenol | 500 | 2 | |
| Comp. Ex. 9 | Pentachlorophenol | 500 | 1 | |
| Comp. Ex. 10 | Pyrogallol | 500 | 1 | |
| Comp. Ex. 11 | Catechol | 500 | 1 | |
| Comp. Ex. 12 | Guaiacol | 500 | 1 | |
| Comp. Ex. 13 | Biphenol | 500 | 4 | |
| Comp. Ex. 14 | Bisphenol | 500 | 3 | |
| Comp. Ex. 15 | Triphenylphosphite | 500 | 1 | |
| Comp. Ex. 16 | Acetylurea | 500 | 2 | |
| Comp. Ex. 17 | Thiourea | 500 | 2 | |
| Comp. Ex. 18 | Barbituric acid | 500 | 1 | |
| Comp. Ex. 19 | Formamide | 500 | | 4 |
| Comp. Ex. 20 | N-butyl isocyanate | 500 | 1 | |
| Comp. Ex. 21 | P-toluene sulfonamide | 500 | 1 | |
| Comp. Ex. 22 | Carbon dioxide | 500 | 1 | |
| Comp. Ex. 23 | Hydrogen sulfide | 500 | | 1 |
| Comp. Ex. 24 | Trichloroacetyl isocyanate | 500 | | 3 |
| Comp. Ex. 25 | Benzoyl chloride | 500 | | 4 |
| Comp. Ex. 26 | Dodecylmercaptan | 500 | 3 | |
| Comp. Ex. 27 | Trifluoromethane-sulfonic acid | 500 | | 1 |
| Comp. Ex. 28 | Triethylamine | 500 | 1 | |
| Comp. Ex. 29 | Siloxane | 500 | 1 | |
| Comp. Ex. 30 | Bis(tributyltin) oxide | 500 | 1 | |
| Comp. Ex. 31 | Hydrogen chloride | 100 | | 10 |

TABLE 2

| No. | Isocyanate compound | Amount of phenol added (ppm) | Days until appearance of turbidity | APHA value on 6th day | Purity (%) Before test | Purity (%) On 6th day |
|---|---|---|---|---|---|---|
| Comp. Ex. 32 | M-xylylene diisocyanate | 0 | 1 | | 99.8 | |
| Example 4 | | 500 | 7 | 10 | 99.8 | 99.6 |
| Comp. Ex. 33 | Phenyl isocyanate | 0 | >10 | 20 | 99.9 | 98.3 |
| Example 5 | | 500 | >10 | 10 | 99.9 | 98.8 |
| Comp. Ex. 34 | 4,4'-Diphenylmethane | 0 | 2 | | 99.8 | |
| Example 6 | diisocyanate | 500 | >10 | 10 | 99.8 | 98.2 |
| Comp. Ex. 35 | Isophorone diisocyanate | 0 | >10 | 40 | 99.9 | 98.6 |
| Example 7 | | 500 | >10 | 10 | 99.9 | 99.7 |
| Comp. Ex. 36 | Thiodiethylene | 0 | >10 | 30 | 99.9 | 98.4 |
| Example 8 | diisocyanate | 500 | >10 | 10 | 99.9 | 99.7 |
| Comp. Ex. 37 | Diphenylsulfide-2,4'- | 0 | 2 | | 99.8 | |
| Example 9 | diisocyanate | 500 | >10 | 10 | 99.8 | 98.4 |
| Comp. Ex. 38 | 1-Isocyanato-3-iso- | 0 | >10 | 30 | 99.8 | 97.9 |
| Example 10 | thiocyanato-propane | 500 | >10 | 10 | 99.8 | 99.6 |
| Comp. Ex. 39 | 2,5(or 6)-Bis(isocyanato- | 0 | 3 | | 99.9 | |
| Example 11 | methyl)bicyclo-[2.2.1]heptane | 500 | >10 | 10 | 99.9 | 99.7 |
| Comp. Ex. 40 | Hexamethylene | 0 | 4 | | 99.9 | |

TABLE 2-continued

| No. | Isocyanate compound | Amount of phenol added (ppm) | Days until appearance of turbidity | APHA value on 6th day | Purity (%) Before test | Purity (%) On 6th day |
| --- | --- | --- | --- | --- | --- | --- |
| Example 12 | diisocyanate | 500 | >10 | 10 | 99.9 | 99.8 |

We claim:

1. A stabilizing method of an isocyanate compound, which comprises adding 10-5000 ppm of phenol to an isocyanate compound.

2. The method of claim 1, wherein the isocyanate compound is an aliphatic polyisocyanates.

3. The method of claim 1, wherein the isocyanate compound is xylylene diisocyanate.

4. An isocyanate composition comprising an isocyanate compound and phenol in an amount of 10-5000 ppm based on the isocyanate compound.

5. The isocyanate composition of claim 4, wherein the isocyanate compound is an aliphatic polyisocyanates.

6. The isocyanate composition of claim 4, wherein the isocyanate compound is xylylene diisocyanate.

* * * * *